United States Patent [19]

Finch et al.

[11] 4,260,620
[45] Apr. 7, 1981

[54] 2-PYRIDINECARBOXYLIC ACIDS

[75] Inventors: Neville Finch, West Orange; Renat H. Mizzoni, Long Valley, both of N.J.

[73] Assignee: Ciba-Geigy Corporation, Ardsley, N.Y.

[21] Appl. No.: 88,730

[22] Filed: Oct. 26, 1979

Related U.S. Application Data

[63] Continuation of Ser. No. 905,320, May 12, 1978, Pat. No. 4,197,302, which is a continuation-in-part of Ser. No. 890,441, Mar. 27, 1978, Pat. No. 4,202,901, which is a continuation-in-part of Ser. No. 787,718, Apr. 15, 1977, abandoned, which is a continuation-in-part of Ser. No. 663,940, Mar. 4, 1976, abandoned.

[51] Int. Cl.³ .................. C07D 213/55; C07D 213/56; A61K 31/455
[52] U.S. Cl. .................. 424/266; 546/296; 546/298; 546/291
[58] Field of Search .................. 546/291, 298, 296; 424/266

[56] References Cited

U.S. PATENT DOCUMENTS

| 3,873,552 | 3/1975 | Blank et al. | 546/298 |
| 3,935,221 | 1/1976 | Miyano et al. | 546/326 |
| 4,036,965 | 7/1977 | Finch | 546/298 |
| 4,189,489 | 2/1980 | Koeda et al. | 424/266 |
| 4,197,302 | 4/1980 | Finch et al. | 546/291 |

FOREIGN PATENT DOCUMENTS 866977 5/1978 Belgium ..................... 546/298

OTHER PUBLICATIONS

Finch et al., Journal of Medicinal Chemistry, vol. 21, pp. 1269-1274 (1978).

Primary Examiner—Alan L. Rotman
Attorney, Agent, or Firm—Theodore O. Groeger

[57] ABSTRACT

5-Etherified 2-pyridinecarboxylic acids, e.g. those of the formula

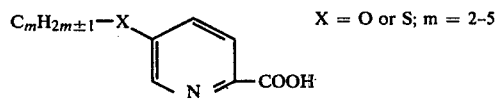

X = O or S; m = 2-5 or functional derivatives thereof, are hypotensive agents.

7 Claims, No Drawings

2-PYRIDINECARBOXYLIC ACIDS

CROSS-REFERENCE TO RELATED APPLICATION

This is a continuation of application Ser. No. 905,320 filed on May 12, 1978, (now U.S. Pat. No. 4,197,302) which is a continuation-in-part of application Ser. No. 890,441, filed Mar. 27, 1978 (now U.S. Pat. No. 4,202,901), which in turn is a continuation-in-part of application Ser. No. 787,718, filed Apr. 15, 1977, which in turn is a continuation-in-part of application Ser. No. 663,940, filed Mar. 4, 1976 (both of which are now abandoned).

BACKGROUND OF THE INVENTION

Fusaric acid, i.e. 4-butyl-2-pyridinecarboxylic acid, the 3- and/or 6-(alkoxy, amino, halo or hydroxy)-derivatives thereof, or halofusaric amides of U.S. Pat. Nos. 3,914,239 or 3,935,221, are known antihypertensive agents, by virtue of their vasodilating and dopamine-$\beta$-hydroxylase inhibitory action, but they also produce tachycardia. Surprisingly, it was found that 2-pyridinecarboxylic acids having a special etherified hydroxy or mercapto group in the 5-position, instead of an alkyl, haloalkyl, alkoxy or cycloalkoxy group therein, which are not dopamine-$\beta$-hydroxylase inhibitors, and produce less tachycardia. Therefore, they are valuable hypotensive agents with minimal cardiac and other side-effects.

SUMMARY OF THE INVENTION

The present invention concerns and has for its object the privison of new 5-etherified 2-pyridinecarboxylic acids and functional derivatives thereof, more particularly of those corresponding to Formula I

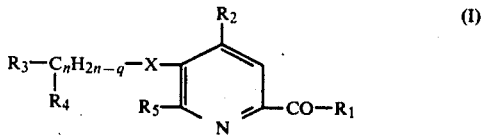

wherein $R_1$ is hydroxy, lower alkoxy, amino, mono- or di-lower alkylamino or hydrazino, $R_2$ is hydrogen, lower alkyl, lower alkoxy or halogeno, X is oxygen or sulfur, $R_3$ is hydrogen, lower alkoxy, lower alkylmercapto, halogeno, amino, mono- or di-lower alkylamino, phenyl or phenyl substituted by one or more than one member selected from lower alkyl, alkoxy or alkylmercapto, halo, trifluoromethyl, cyano, $COR_1$ or amino, $R_4$ is hydrogen, hydroxy or $COR_1$, $R_5$ is $R_2$ or $COR_1$, n is an integer from 1 to 7, q is 1 or 3, (n−q) is positive and in which 5-substituent all heteroatoms and double bonds are separated from each other by at least two carbon atoms, the N-oxide or a therapeutically useful salt thereof, as well as of corresponding pharmaceutical compositions and of methods for the preparation and application of said products, which are useful hypotensive agents in the treatment or management of hypertension in mammals.

DESCRIPTION OF THE PREFERRED EMBODIMENTS

A lower alkoxy or alkylmercapto group $R_1$, $R_2$, $R_3$, $R_5$, or within $R_3$=(alkoxy or alkylmercapto)-phenyl is preferably methoxy or methylmercapto, but also ethoxy, n- or i-propoxy or -butoxy or ethylmercapto. The lower alkyl groups $R_2$ and $R_5$, or those within $R_1$=alkylamino or $R_3$=alkylphenyl, preferably represent methyl, but also ethyl, n- or i-propyl or -butyl. A halogen atom $R_2$, $R_3$, $R_5$, or within $R_3$=halophenyl, is preferably fluoro, chloro or bromo. Accordingly, mono- or di-lower alkylamino groups $R_1$ or $R_3$ represent preferably mono- or di-(methylamino, ethylamino, n- or i-propylamino). A substituted phenyl radical $R_3$ contains preferably up to three, advantageously one or two of said members, such as methyl or ethyl; methoxy or ethoxy; methylmercapto; fluoro, chloro or bromo; trifluoromethyl; amino; or said free, esterified or amidized carboxy groups. The term "lower" referred to above or hereinafter in connection with organic radicals or compounds respectively, defines such with up to 7, preferably up to 4, advantageously with one or two carbon atoms.

In the radical $R_3,R_4$-$C_nH_{2n-q}$, $R_4$ is preferably hydrogen, n is preferably an integer from 1 to 4, and q is 1, thus $C_nH_{2n-q}$ becomes methylene, 1,1- or 1,2-ethylene, 1,1-, 1,2- or 1,3-propylene, 1,1-, 1,2-, 1,3-, 1,4- or 2,3-butylene; provided it separates heteroatoms within $R_3$ from X by at least 2 carbon atoms. In case q is 3, said radical represents preferably 1,3-prop-1-enylene, 1,3-but-1-enylene or 1,4-but-1 or 2-enylene.

The N-oxide is preferably the pyridine-1-oxide of the compounds with X=O, and the salts are preferably therapeutically acceptable alkali metal, e.g. sodium or potassium, salts of the free acids, or acid addition salts of the bases, e.g. those derived from the acids listed below.

The compounds of the invention exhibit valuable pharmacological properties, primarily hypotensive and antihypertensive activity. This is demonstrable in animal tests, using advantageously mammals, e.g. rats, cats or dogs, as test objects. The animals may either be normotensive or hypertensive, e.g. genetically or renal hypertensive rats or dogs. Said compounds can be applied to them enterally or parenterally, advantageously orally, subcutaneously, intravenously, intraperitoneally or intraduodenally, for example within gelatin capsules or in the form of starchy suspensions or aqueous solutions respectively. The applied dosage may range between about 0.1 and 200 mg/kg/day, preferably between about 1 and 100 mg/kg/day, advantageously between about 5 and 50 mg/kg/day. The lowering effect on the blood pressure is recorded either directly by means of a catheter, e.g. placed in the rat's caudal or dog's femoral artery, and a transducer, expressing the blood pressure prior and after dosing in mm/Hg, or indirectly by sphygmomanometry, e.g. at the rat's tail. Thus, for example, the 5-(m-chlorobenzylmercapto)-pyridine-2-carboxylic acid, or the 5-($\alpha$-n-propyl-m-trifluoromethylbenzylmercapto)-pyridine-2-carboxylic acid, two representative members of the compounds of the invention are very effective in said tests, the latter is even slowing the heart rate. Accordingly, the compounds of the invention are useful antihypertensive agents in the treatment or management of essential or renal hypertension in mammals. They are also useful intermediates in the preparation of other valuable products, especially of pharmacologically active compositions.

Particularly useful are compounds of Formula I, in which $R_1$ is hydroxy, lower alkoxy, amino, mono- or di-lower alkylamino or hydrazino, each of $R_2$ and $R_5$ is hydrogen, lower alkyl, lower alkoxy or halogeno, X is oxygen or sulfur, and $R_3R_4C_nH_{2n-q}$ is lower alkyl or alkenyl with up to 7 carbon atoms, preferably ethyl, n- or i-propyl, butyl or -pentyl, or t-butyl or -pentyl; allyl, methallyl, 2- or 3-butenyl or -pentenyl, or a therapeutically useful ammonium, alkali metal or acid addition salt thereof.

Outstanding compounds of the invention are those of Formula II

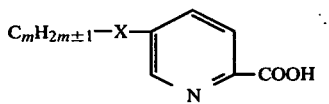

wherein m is an integer from 2 to 5 and X is oxygen or sulfur, or a therapeutically useful ammonium, alkali metal or acid addition salt thereof.

Most preferred are the compounds of Formula II, wherein $C_mH_{2m\pm1}$ is n-or i-propyl or -butyl, allyl or methallyl and X is oxygen or sulfur, or a therapeutically useful ammonium, alkali metal or acid addition salt thereof.

The compounds of the invention are prepared according to methods known per se, advantageously by:

(1) hydrolyzing the nitrile of Formula III

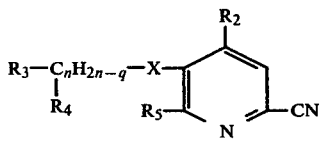

to the corresponding acid or amide and, if desired, converting any resulting compound into another compound of the invention. Said hydrolysis is performed according to known methods, preferably with aqueous acids or bases, such as strong mineral or carboxylic acids, or alkali metal hydroxides respectively, e.g. hydrochloric sulfuric, perchloric or acetic acid; sodium or potassium hydroxide, advantageously in the presence of lower alkanols, e.g. methanol or ethanol.

Another process for preparing the compounds of Formula I consists in:

(2) oxidizing the aldehyde of Formula IV

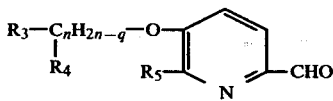

to the corresponding acid and, if desired, converting any resulting compound into another compound of the invention. Said oxidation is also preformed according to standard oxidation methods, for example, with the use of air, pure or electrolytically generated oxygen, preferably in the presence of heavy metal catalysts, such as silver, manganese, cobalt, platinum or palladium catalysts, or with oxidation agents, e.g. hydrogen peroxide or nitric oxides, oxidizing acids or their salts, such as hypohalous, periodic, nitric or percarboxylic acids or suitable salts thereof, e.g. sodium hypochlorite or periodate; peracetic, perbenzoic or monoperphthalic acid; heavy metal salts or oxides, such as alkali metal chromates or permanganates, chromic or cupric salts, e.g. halides or sulfates thereof, or silver, mercuric, chromium VI or manganese IV oxide, in acidic or alkaline media respectively. In such oxidations, the conditions and starting materials are so chosen that no other oxidations will occur within the molecule, e.g. a hydroxy group $R_4$ oxidized to oxo or a double bond (q=3) epoxidized, unless it is desired that such unsaturated compound is converted via the epoxide or other derivative into another compound of the invention as described below. Otherwise, said hydroxy group may be protected during oxidation, for example, by acylation with a lower alkanoic acid halide or anhydride, or by etherification with a reactive ester of an α-aralkanol, e.g. benzyl chloride, and the oxidized acyl- or aralkyl-derivative hydrolyzed or hydrogenolyzed with aqueous alkali metal hydroxides, or catalytically activated hydrogen respectively.

The compounds of the invention can also be prepared by:

(3) condensing compounds of Formulae V and VI

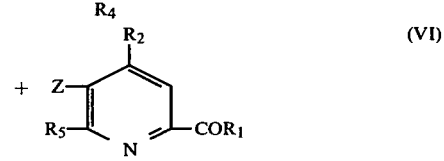

wherein one of Y and Z is free or metallized XH and the other is XH esterified with a strong, inorganic or organic acid, preferably a hydrohalic, e.g. hydrochloric, -bromic or -iodic acid, or an alkane or benzene sulfonic acid, e.g. methane, p-toluene or m-bromobenzene sulfonic acid; or Y is XH and Z is nitro and, if desired, converting any resulting compound into another compound of the invention. Said condensation is carried out either with the free enols and said esters in the presence of basic condensation agents, such as alkali metal or alkaline earth metal hydrides, hydroxides, carbonates or bicarbonates or organic nitrogen bases, e.g. tri-lower alkylamines, pyridines or quinolines; or preferably with alkali metal salts of said enols in aprotic solvents, e.g. dimethylformamide or -sulfoxide. The latter, as well as alkali metal hydrides, are advantageously employed in the condensation with $Z=NO_2$.

The compounds of the invention so obtained can be converted into each other according to known methods. For example, resulting free acids can be esterified with lower alkanols in the presence of said strong acids, or with diazo-lower alkanes, or converted into their halides by treatment with thionyl halides, or phosphorus halides or oxyhalides. Resulting esters may be hydrolyzed or transesterified in the presence of said alkaline or acidic agents respectively, or said esters or halides treated with ammonia, mono- or di-lower alkylamines or hydrazine, in order to obtain the amides or hydrazides. These, in turn, can be hydrolyzed or alcoholized under acidic or alkaline conditions. Resulting unsaturated compounds (q=3 and $R_4$=H) can be hydrohalogenated, hydrated or halogenated and any resulting mono- or bishalide treated with alkali metal lower alkoxides or mercaptides, ammonia, mono- or di-lower alkylamines and/or alkali metal hydroxides, in order to obtain compounds with $R_3$ being lower alkoxy, lower alkylmercapto, amino, mono- or di-lower alkylamino and $R_4$ being hydrogen or hydroxy. Furthermore, said compounds of Formula I can be N-oxidized, for example, with ozone, hydrogen peroxide, inorganic or preferably organic peracids, such as persulfuric, lower alkanoic or benzoic peracids, e.g. peracetic or perbenzoic acid; or resulting N-oxides reduced, either with catalytically activated hydrogen or phosphorus halides.

Finally, a resulting acid can be converted into its salts according to conventional methods, for example, by reacting it with a stoichiometric amount of a suitable salt-forming reagent, such as ammonia or an alkali metal hydroxide, carbonate or hydrogen carbonate. A salt of their type can be reconverted into the free acid by treatment with an acid, e.g. hydrochloric, sulfuric or acetic acid, until the proper pH has been reached. A resulting basic ompound can be converted into a corresponding acid addition salt, for example, by reacting it with an inorganic or organic acid, preferably a therapeutically useful acid, or with a corresponding anion exchange preparation, and isolating the desired salt. An acid addition salt may be converted into the free compound by treatment with a base, e.g. a metal hydroxide, ammonia or a hydroxylion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, pamoic, nicotinic, methanesulfonic, ethanesulfonic, hydroxyethanesulfonic, ethylenesulfonic, benzenesulfonic, halobenzenesulfonic, toluenesulfonic, naphthalenesulfonic, sulfanilic or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-camphor sulfonates or d-$\alpha$-(1-naphthyl)-ethylamine or l-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. For example, in the above-described oxidation methods, the aldehydes IV are formed intermediately from the corresponding 2-carbinols under the applied conditions. In the process of the invention, those starting materials are advantageously selected, which yield the above-described preferred embodiments thereof, especially those corresponding to Formula II.

The starting material used is known or, if new, may be prepared according to methods described for known analogs thereof and those illustrated by the examples herein. Thus, for example, the aldehydes IV are obtained from corresponding 2-methyl-pyridines which are oxidized with hydrogen peroxide to give the corresponding N-oxide. The latter is rearranged with acetic anhydride and aqueous hydrochloric acid to the corresponding 2-carbinol, which is then oxidized with potassium permanganate to the desired aldehyde IV. It can be converted into the corresponding oxime, the latter dehydrated with methanesulfonyl chloride or acetic anhydride, to yield the nitriles III.

Esters of Formula VI are obtained according to the following steps: 5-hydroxy-2-pyridinemethanols are etherified with benzyl chloride in the presence of sodium hydride to give the corresponding 5-benzyl ethers, which are then oxidized with potassium permanganate to the corresponding acids, which are esterified, e.g. to the corresponding methyl esters, which in turn are hydrogenolysed to give the esters VI, which may be hydrolyzed to the acids or converted to the amides or hydrazides VI as shown for I above. Compounds VI with Z=SH can be prepared from 5-amino-2-pyridinecarboxylic acid esters by diazotization, reacting the diazonium salt with potassium and cuprous thiocyanate followed by reducing the resulting 5-thiocyanate with sodium borohydride.

Most of the starting materials V are commercially available as, for example, lower alkyl or allyl halides, especially bromides and various other reactive esters, and the preparation of a few new members thereof is illustrated by the examples herein.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserviing, stabilizing, wetting or emulsifying agents, solution promoters, salts for regulating the osomotic pressure and/or buffers. They may also contain other therapeutically valuable substances. Said pharmaceutical compositions are prepared according to conventional mixing, granulating or coating methods respectively and contain about 0.1 to 75% preferably about 1 to 50% of the active ingredient.

The following examples, illustrating the invention, are not to be construed as being limitations thereof. Temperatures are given in degrees Centigrade, all parts wherever given are parts by weight and, if not otherwise stated, all evaporations are carried out under reduced pressure, e.g. between about 0.1 and 15 mmHg.

EXAMPLE 1

The mixture of 13.1 g of 5-(m-chloro-benzyloxy)-2-pyridinemethanol and 250 ml of water is stirred vigorously at 25°. To this mixture is added 11.5 g of potassium permanganate in several portions. Then the mixture is filtered, the precipitated manganese dioxide washed with hot water, the washing is combined with the filtrate, concentrated to a small volume and then acidified with aqueous hydrochloric acid. The precipitated product is collected and recrystallized from ethyl acetate to yield 5-(3-chloro-benzyloxy)-2-pyridinecarboxylic acid melting at 176°–177°.

The starting material is prepared as follows:

A mixture of 100.0 g of 2-methyl-5-hydroxy-pyridine, 600 ml of acetic acid and 200 ml of 30–35% hydrogen peroxide is heated on a steam bath with occasional swirling for 18 hours. Then to the mixture is added 500 ml of water and the resulting solution is evaporated to leave a residue. The last traces of water from the residue are removed azeotropically with isopropanol to give a yellow solid. This solid is recrystallized from ethanol to give 2-methyl-5-hydroxy-pyridine-1-oxide melting at 185°–187°.

82 g of the above oxide is added in portions to 66 ml of acetic anhydride at 70°–80° and then the mixture is heated at 70°–75° for 5 hours. After that, the solution is evaporated and the residue is extracted with ether. The ether extract is washed with water, dried over sodium sulfate and filtered. The ether is distilled off and the residue is distilled to yield 2-acetoxymethyl-5-acetoxypyridine, boiling at 123°–125°/0.5 mm.

220.0 g of the above ester is added to 2,200 ml of 6N-hydrochloric acid and the resulting solution is refluxed for 18 hours. Then, the solution is evaporated to leave an oily viscous residue. This residue is digested with ethyl methyl ketone to yield 5-hydroxy-2-pyridinemethanol hydrochloride melting at 122°–123°. (The corresponding free base is prepared by adding a saturated solution of potassium carbonate to the hydrochloride, extracting the resulting suspension with chloroform, drying the chloroform extract over sodium sulfate, filtering and evaporating the filtrate to yield the free base.)

The solution of 16.2 g of 5-hydroxy-2-pyridinemethanol hydrochloride in 150 ml of methaol is added to a solution of 4.6 g of sodium in 250 ml of methanol, while stirring, over a period of 25 minutes. The solution is stirred for one hour and then a solution of 19.3 g of m-chlorobenzyl chloride in 50 ml of methanol is added. Then the mixture is refluxed for 19 hours, cooled, filtered and the filtrate evaporated to a residue. The residue is suspended in 100 ml of water, made basic with 20% aqueous sodium hydroxide solution and then extracted with chloroform. The chloroform extract is separated, dried over sodium sulfate, filtered and the filtrate evaporated, to yield 5-(m-chlorobenzyloxy)-2-pyridinemethanol melting at 78°–80°.

Analogously is prepared B 5-benzyloxy-2-pyridinemethanol boiling at 125°–145°/0.25 mmHg and 5-(4-chlorobutoxy)-2-pyridinemethanol hydrochloride melting at 123°; from corresponding starting materials.

Other starting materials may be prepared as follows:

The solution of 32.7 g of 2-methyl-5-hydroxy-pyridine in 300 ml of dimethylformamide is added to a suspension of 12.8 g of sodium hydride (57% mineral oil dispersion) in 150 ml of dimethylformamide, with stirring. Then the mixture is heated to 100° and maintained at 100° for 18 hours. After that, the mixture is cooled to room temperature and to the cooled mixture is added a solution of 49.8 g of benzyl chloride in 100 ml of dimethylformamide over a period of 30 minutes. The mixture is then refluxed for 7 hours, cooled and then evaporated to a residue. The residue is partitioned between water and ether, the layers are separated and the water layer extracted with ether. The ether layer is combined with ether extract, dried over sodium sulfate, filtered and the ethereal filtrate is distilled off. The residue is distilled to yield 5-benzyloxy-2-methyl-pyridine, boiling at 100°–102°/0.02 mm/Hg.

Analogously is prepared the following compound: 5-(2-ethoxyethoxy)-2-methyl-pyridine, boiling at 135°–137°/15 mm/Hg.

The above compounds are taken through the same sequence of steps described previously to yield the corresponding 2-pyridinemethanols, listed below: 5-benzyloxy-2-pyridinemethanol, boiling at 125°–145°/0.25 mm/Hg and 5-(2-ethoxyethoxy)-2-pyridinemethanol, boiling at 115°–120°/0.55 mm/Hg.

Following the oxidation procedure described previously, the following compounds are obtained from the corresponding methanols:

5-benzyloxy-2-pyridinecarboxylic acid, melting at 143°–145°;

5-(2-ethoxyethoxy)-2-pyridinecarboxylic acid, melting at 115°–116°;

5-(4-chlorobutoxy)-2-pyridinecarboxylic acid, melting at 95°–97°.

EXAMPLE 2

A mixture of 9.0 g of 5-(3-chloropropoxy)-2-pyridinecarboxylic acid methyl ester and 100 ml of 6N-hydrochloric acid is heated on a steam bath for 30 minutes. After that, the solution is cooled and evaporated to a residue. To the residue is added water and the resulting suspension is adjusted to pH 5 with saturated aqueous solution of sodium bicarbonate. The precipitated product is collected, dissolved in ethyl acetate and filtered. The filtrate is evaporated to a small volume. To the concentrate is added hexane to yield 5-(3-chloropropoxy)-2-pyridinecarboxylic acid melting at 120°–121°.

The starting material is prepared as follows:

The solution of 13.8 g of 5-hydroxy-2-pyridinecarboxylic acid methyl ester in 200 ml of dimethylformamide is added over a period of 45 minutes to a suspension of 4.3 g of sodium hydride in (57% mineral oil dispersion) 50 ml of dimethylformamide with stirring at room temperature. The mixture is stirred at room temperature for one hour and then is cooled to 5°–10°. To this cooled mixture is added a solution of 19.3 g of 1-bromo-3-chloropropane in 100 ml of dimethylformamide. The mixture is heated to 45°–50° and stirred at 45°–50° for 4 hours and 30 minutes. After that, the mixture is cooled, filtered and the filtrate evaporated to a residue. The residue is partitioned between methylene chloride and water and the layers are separated. The methylene chloride layer is washed with water and dried over anhydrous sodium sulfate. The methylene chloride solution is filtered and the filtrate evaporated to yield 5-(3-chloropropoxy)-2-pyridinecarboxylic acid methyl ester.

Alternatively, 5-(3-chloropropoxy)-2-pyridinecarboxylic acid may be prepared as follows:

The mixture of 30.0 g of 5-(3-chloropropoxy)-2-pyridine methanol and 1,200 ml of water is stirred vigorously at 5°. To this mixture is added 31.0 g of potassium permanganate in several portions during which time the temperature of the mixture rises to 25° and then the mixture is stirred at 25° for 30 minutes. Then the mixture is filtered, the precipitated manganese dioxide washed with several portions of water, the washing is combined with the filtrate and the resulting aqueous solution is adjusted to pH 5. Then the aqueous solution is evaporated to a small volume and the concentrate is extracted several times with ethyl acetate. After the extracts are combined, the combined ethyl acetate solution is washed and dried. The solution is filtered and the filtrate evaporated to yield 5-(3-chloropropoxy)-2-pyridinecarboxylic acid melting at 120°-121°.

The starting material is prepared as follows:

To the stirred solution of 32.32 g of 5-hydroxy-2-pyridinemethanol hydrochloride in 200 ml of dimethylformamide is added 18.2 g of sodium hydride (50% mineral oil dispersion) in portions while maintaining a temperature of 50°-55° of the mixture. Then the mixture is stirred at 50°-55° for 30 minutes and then is added a solution of 31.5 g of 1-bromo-3-chloropropane in 50 ml of dimethylformamide, while maintaining a temperature below 50° of the mixture. After that, the mixture is allowed to come to room temperature and is additionally stirred at room temperature for 2 hours and 30 minutes. Then the mixture is poured into 1,200 ml of water, the aqueous mixture is saturated with sodium chloride and the resulting saturated solution extracted three times with ether. The ether extracts are combined, the combined ether solution is washed and dried over anhydrous magnesium sulfate. The ether solution is filtered and the filtrate evaporated to yield 5-(3-chloropropoxy)-2-pyridinemethanol.

EXAMPLE 3

4.7 g of 5-hydroxy-2-pyridinecarboxylic acid methyl ester is added to a stirred suspension of 1.30 g of sodium hydride (57% mineral oil dispersion) in 10 ml of dimethylformamide at room temperature while maintaining a nitrogen atmosphere. The mixture is stirred for 30 minutes and then is added a solution of 3.90 g of allyl bromide in 20 ml of dimethylformamide. The mixture is heated to 100° and maintained at 100° for 5 hours. Then the mixture is cooled, filtered and the filtrate evaporated to a residue. The residue is partitioned between water and methylene chloride, the layers are separated and the water layer is extracted with methylene chloride. The methylene layer is combined with the methylene extract, dried over anhydrous sodium sulfate and filtered. The filtrate is evaporated and the residue is distilled to yield 5-allyloxy-2-pyridinecarboxylic acid methyl ester boiling at 124°-130°/0.15 mm/Hg.

The starting material is prepared as follows:

The solution of 2.8 g of 5-benzyloxy-2-pyridinemethanol in 200 ml of benzene is added to 23.0 g of activated manganese dioxide at room temperature. The suspension is stirred for 1 hour and then evaporated to a residue. The residue is dissolved in 150 ml of methanol and then added to 23.0 g of activated manganese dioxide and 3.28 g of sodium cyanide. After that, 1.2 g of acetic acid is added to the mixture and the mixture is stirred for 16 hours at room temperature. The mixture is filtered, the precipitated solids washed with methanol, the methanol washing is combined with the filtrate and then evaporated to a residue. The residue is recrystallized from isopropanol to yield 5-benzyloxy-2-pyridinecarboxylic acid methyl ester melting at 90°-90.5°.

A mixture of 7.9 g of 5-benzyloxy-2-pyridinecarboxylic acid methyl ester, 100 ml of 75% aqueous ethanol and 0.2 g of palladium over carbon (5%) is hydrogenated at 47 psi at room temperature. After the theoretical uptake of hydrogen, the mixture is filtered and the filtrate evaporated to yield 5-hydroxy-2-pyridinecarboxylic acid methyl ester melting at 191.5°-192.5°.

EXAMPLE 4

To the suspension of 0.67 g of 5-allyloxy-2-pyridinecarboxylic acid methyl ester in 2 ml of water is added 0.552 g of n-bromo-acetamide. To the suspension is then added 4.0 ml of 1-N-sulfuric acid and the resulting solution is stirred at room temperature for 25 minutes and additionally stirred at 30° for 30 minutes. To the solution is added 0.42 g of sodium bisulfate and the solution is neutralized with sodium carbonate to pH 6-7. Then the solution is saturated with sodium carbonate and extracted with methylene chloride. The combined methylene chloride extracts are dried over sodium sulfate, filtered and the filtrate evaporated to give an oily residue. This oil is dissolved in 5 ml of ethanol and 1.1 ml of isopropylamine and the resulting solution is stirred for 25 minutes at room temperature. Then to the solution is added 0.2 g of potassium hydroxide in 3 ml of anhydrous methanol and the resulting mixture is heated to 45° and maintained for 4 hours, during which time an additional above equal amount of isopropylamine is added. After that, the mixture is allowed to cool to room temperature, and stirred for 12 hours at room temperature. The mixture is evaporated and the residue is partitioned between water and methylene chloride. The layers are separated and the methylene chloride layer is dried over sodium sulfate, filtered and the filtrate evaporated to a residue. The residue is dissolved in ethyl acetate and then acidified with a solution of anhydrous hydrochloric acid in ethyl acetate to pH 2, to yield 5-(3-isopropylamino-2-hydroxy)propoxy-2-pyridinecarboxylic acid methyl ester hydrochloride melting at 194°.

EXAMPLE 5

To a solution of 2.4 g of 5-benzyloxy-2-pyridinecarboxylic acid methyl ester in 75 ml of methanol is added a solution of 1.0 g of hydrazinehydrate in 30 ml of methanol. The resulting solution is refluxed for 7 hours, cooled and then concentrated to a small volume. The concentrate is chilled in an ice bath and the precipitated product is collected on a filter and washed. This product is recrystallized from ethanol to yield 5-benzyloxy-2-pyridinecarbohydrazide melting at 140°-142°.

EXAMPLE 6

A mixture of 3.0 g of 5-(3-chloro-2-butenyloxy)-2-pyridinecarboxylic acid methyl ester and 30 ml of 6N-hydrochloric acid is heated on a steam bath for one hour. After that, the solution is cooled and the pH is adjusted to 5-6. Then the solution is evaporated and the residue extracted with ethanol. The ethanol extract is evaporated to yield 5-(3-chloro-2-butenyloxy)-2-pyridinecarboxylic acid melting at 96°-98°.

The starting material is prepared as follows:

The solution of 4.7 g of 5-hydroxy-2-pyridinecarboxylic acid methyl ester in 50 ml of dimethylformamide is added over a period of 30 minutes to a suspension of 1.3 g of sodium hydride in (57% mineral oil dispersion) 50 ml of dimethylformamide at 20°, with stirring. The mixture is stirred at 20° for one hour and then is added dropwise 4.11 g of dichlorobutene. The mixture is heated to 50° and stirred at 50° for 3 hours. After that, the mixture is cooled, filtered and the filtrate evaporated to a residue. The residue is dissolved in the water and extracted with methylene chloride. The methylene chloride extract is washed with water and dried over anhydrous sodium sulfate. The methylene chloride solution is filtered and the filtrate evaporated to yield 5-(3-chloro-2-butenyloxy)-2-pyridinecarboxylic acid methyl ester.

EXAMPLE 7

The solution of 2.3 g of 5-n-butylmercapto-2-pyridinecarbonitrile in 15 ml of 20% potassium hydroxide plus 15 ml of methanol is refluxed for one hour. Then the solution is cooled and the methanol is distilled off under reduced pressure. The residual aqueous layer is washed once with ether, and then the pH of the aqueous layer is adjusted to 6–7. Then the aqueous solution is extracted three times with ether, the ether extracts are combined, the combined ethereal solution is washed with water and then dried over anhydrous magnesium sulfate. The ethereal solution is filtered and the filtrate evaporated to give a solid. This solid is recrystallized from ethanol to yield 5-n-butylmercapto-2-pyridinecarboxylic acid melting at 100°–102°.

The starting material is prepared as follows:

15.8 g of pyridine is added to an ethereal solution of methyl lithium, while stirring and maintaining a nitrogen atmosphere. The mixture is stirred for 16 hours at room temperature and then a solution of 13.5 g of n-butyldisulfide in 100 ml of tetrahydrofuran is added dropwise to the mixture. Then the mixture is stirred for 6 hours at room temperature. The mixture is diluted with a mixture of ether plus water and the organic phase separated. The organic layer is washed with a saturated solution of potassium chloride, dried over anhydrous magnesium sulfate, filtered and the filtrate evaporated to an oil. This oil is dissolved in ether and the ethereal solution extracted twice with 4N-sulfuric acid. The aqueous acidic layer is separated, cooled in ice, is made basic and the basic solution is extracted twice with ether. The ethereal extracts are combined, the combined ethereal solution is washed, dried over anhydrous magnesium sulfate, filtered and the filtrate evaporated to an oil. This oil is distilled to yield 5-n-butylmercapto-2-methyl-pyridine boiling at 77°–91°/0.1 mm/Hg.

A solution of 10.8 g of the above n-butylmercapto-pyridine in 80 ml of tetrahydrofuran is added to a 0.5 M aqueous solution of sodium m-periodate, with stirring. The solution is stirred at room temperature for 16 hours and then evaporated to give a semi-solid residue. The residue is dissolved in a mixture of ether plus water, the layers are separated and the aqueous layer extracted three times with ether. The ethereal layer is combined with the ether extracts, and the resulting ethereal solution is washed with a saturated solution of potassium chloride. The ethereal solution is dried over anhydrous magnesium sulfate, filtered and the filtrate evaporated to give 5-n-butylmercapto-2-methyl-pyridinesulfoxide.

A solution of 7.5 g of the above sulfoxide in 60 ml of tetrahydrofuran is added to a solution of 14.0 g of potassium tertiary butoxide in tetrahydrofuran, while stirring and maintaining a nitrogen atmosphere. The solution is stirred for 2 hours at room temperature, cooled to 5° in an ice bath and then a solution of 14.6 g of isoamyl nitrite in 30 ml of tetrahydrofuran is added to the solution all in one portion. The temperature of the solution is allowed to rise to room temperature and the solution is additionally stirred at room temperature for 16 hours. After that, the solution is evaporated and the residue is dissolved in a mixture of ether plus water. The ethereal layer is separated and the aqueous layer is extracted once with ether. The aqueous layer is acidified to a pH of 2, extracted with ether and then the pH of the aqueous solution is adjusted to 6.8–7. The aqueous solution is saturated with sodium chloride and the saturated solution is extracted three times with ether. The ether extracts are combined, washed and dried over anhydrous magnesium sulfate. The ether solution is filtered and the filtrate evaporated to yield a solid. This solid is recrystallized from ether to give an oxime of 5-n-butylmercapto-2-pyridinecarboxaldehydesulfoxide melting at 90°–91°.

To a stirred ice bath cold solution of 12.0 g of the above oxime in 80 ml of pyridine is added 7.3 g of methanesulfonyl chloride all in one portion. Then the mixture is additionally stirred for 2 hours at the ice bath temperature, the temperature is allowed to rise to room temperature and the mixture is further stirred for 14 hours at room temperature. The mixture is evaporated and the residue is suspended in water, the aqueous suspension is basified with potassium bicarbonate and then extracted four times with ether. The ether extracts are combined, washed with a saturated solution of potassium chloride and then dried over anhydrous magnesium sulfate. The ethereal solution is filtered and the filtrate evaporated to an oil. This oil is crystallized from isopropanol to give 5-n-butylmercapto-2-pyridinecarbonitrilesulfoxide melting at 54°–55°.

The solution of 3.7 g of the above nitrile in 40 ml of trifluoroacetic anhydride is refluxed for 2 hours on a steam bath. Then this solution is evaporated and the residue is dissolved in ether. The ethereal solution is washed with 2% solution of potassium bicarbonate followed by a saturated solution of potassium chloride. The ethereal solution is dried over anhydrous magnesium sulfate, filtered and the filtrate evaporated to give 5-(1-trifluoroacetoxy)-n-butylmercapto-2-pyridinecarbonitrile.

A solution of 4.45 g of 5-(1-trifluoroacetoxy)-n-butylmercapto-2-pyridinecarbonitrile in anhydrous ethanol is added with stirring to a solution of 0.345 g of sodium in ethanol. After that, the mixture is stirred for 1 hour at room temperature and then a solution of 2.6 g of n-butyl bromide in 8 ml of ethanol is added to the mixture. Then the mixture is heated to 70° and maintained at 70° for 16 hours. The mixture is cooled and then evaporated to a residue. The residue is dissolved in ether, the ethereal solution washed with water, then with a saturated solution of potassium chloride and dried over anhydrous magnesium sulfate. The ethereal solution is filtered and the filtrate evaporated to give a 5-n-butylmercapto-2-pyridinecarbonitrile.

Analogously are prepared the following compounds from corresponding alkyl or aryl halides:

5-o-chlorobenzylmercapto-2-pyridinecarbonitrile;
5-p-chlorobenzylmercapto-2-pyridinecarbonitrile;
5-benzylmercapto-2-pyridinecarbonitrile;
5-phenethylmercapto-2-pyridinecarbonitrile;
5-m-trifluoromethylbenzylmercapto-2-pyridinecarbonitrile;
5-m-fluorobenzylmercapto-2-pyridinecarbonitrile;

5-(3-chloropropylmercapto)-2-pyridinecarbonitrile.

EXAMPLE 8

4.0 g of 5-m-chlorobenzylmercapto-2-pyridinecarbonitrile is suspended in 4 N-hydrochloric acid and the resulting suspension is refluxed for 22 hours. The acidic solution is extracted twice with ether and the combined ether extracts are washed twice with 10% potassium bicarbonate solution. The potassium bicarbonate washes are combined, acidified, and the precipitated solid is collected on a filter and washed with water. The solid is recrystallized from isopropanol to give 5-m-chlorobenzylmercapto-2-pyridinecarboxylic acid melting at 156°–158°.

The starting material is prepared as follows:

6.3 g of 5-(1-trifluoroacetoxy)-n-butylmercapto-2-pyridinecarbonitrile (prepared as described previously) is dissolved in ethanol and the resulting solution is then added to a stirred solution of sodium ethoxide in ethanol. The solution is stirred for 1.3 hours at room temperature and then a solution of m-chlorobenzyl chloride in ethanol is added to the solution all in one portion. The solution is then warmed to 70° and maintained at 70° for 16 hours. After that, the solution is evaporated and the residue is dissolved in ether. The ethereal solution is washed twice with water, dried over anhydrous magnesium sulfate, filtered and the filtrate evaporated to give 5-m-chlorobenzylmercapto-2-pyridinecarbonitrile.

EXAMPLE 9

To the stirred suspension of 1.73 g of sodium hydride in 30 ml of dimethylformamide the solution of 12.7 g of m-chlorobenzylmercaptan is added during 2 minutes and stirring is continued for 15 minutes. Thereupon the solution of 12.25 g of 5-nitro-pyridine-2-carboxylic acid methyl ester in 75 ml of dimethylformamide is added all at once. The mixture is stirred for 1 hour on the steam bath and allowed to stand at room temperature overnight. It is poured onto ice and acetic acid, the suspension obtained filtered and the residue recrystallized from 95% aqueous ethanol, to yield the 5-(m-chlorobenzylmercapto)-2-pyridinecarboxylic acid methyl ester melting at 75°–77°.

The starting material is prepared as follows: 250 g of m-chlorobenzyl chloride, 16.6 g of potassium thiocyanate and 150 ml of 95% aqueous ethanol is refluxed for 3 hours and evaporated. The residue is taken up in methylene chloride and water, the organic solution separated, washed with water, dried and evaporated to yield the m-chlorobenzyl thiocyanate.

The solution of 27.1 g thereof in the minimum amount of diethyl ether is added dropwise to the suspension of 6.7 g lithium aluminumhydride in 50 ml of diethyl ether while stirring and the mixture is refluxed for 90 minutes. The excess reagent is destroyed with saturated aqueous potassium sodium tartrate, the mixture filtered and the filtrate washed with water. It is dried and evaporated, to yield the m-chlorobenzylmercaptan. Analogously the m-trifluoromethylbenzylmercaptan is prepared.

EXAMPLE 10

To the stirred suspension of 1.08 g of sodium hydride in 25 ml of dimethylformamide the solution of 9.0 g of m-trifluoromethylbenzylmercaptan in 50 ml of dimethylformamide is added during 3 minutes and the mixture stirred for 10 minutes. It is combined with 7.75 g of 6-methyl-5-nitropyridine-2-carboxylic acid methyl ester and the whole stirred on the steam bath for 30 minutes and allowed to stand overnight at room temperature. 2 ml of acetic acid are added and the solution is mixed with ice water to produce a dense, grainy precipitate. It is filtered off and recrystallized from isopropanol-diethyl ether, to yield the 6-methyl-5-(m-trifluoromethylbenzylmercapto)-pyridine-2-carboxylic acid methyl ester melting at 91°–93°.

6 g thereof are dissolved in methanol-water (1:4), 2.5 ml of N aqueous sodium hydroxide are added and the solution is warmed on a steam bath for ½ hour and allowed to stand at room temperature overnight. The mixture is washed with diethyl ether and the aqueous phase acidified with 2 N hydrochloric acid. The precipitate formed is collected and recrystallized from aqueous methanol, to yield the corresponding acid melting at 100°–105°.

EXAMPLE 11

To the solution prepared from 80 ml of methanol and 0.89 g of sodium, 6.53 g of 5-mercaptopyridine-2-carboxylic acid methyl ester are added, followed by the solution of 12.6 g of methyl α-bromo-m-trifluoromethylphenylacetate in 50 ml of methanol while stirring under nitrogen. The mixture is warmed for ½ hour on the steam bath and allowed to stand at room temperature overnight. It is evaporated, the residue taken up in water-diethyl ether, the organic phase washed with water, dried and evaporated. The residue is dissolved in the minimum amount of methanol-isopropanol (1:1), the solution mixed with 85 ml of N aqueous sodium hydroxide, warmed for ½ hour on the steam bath, and stored at room temperature overnight. The mixture is evaporated, the residue taken up in 2 N hydrochloric acid and the mixture extracted with diethyl ether-ethyl acetate (1:1). The extract is washed with water, dried and evaporated and the residue recrystalized from diethyl ether-ethyl acetate, to yield the 5-(α-carboxy-m-trifluoromethylbenzylmercapto)-pyridine-2-carboxylic acid melting at 190°–195°.

The starting material is prepared as follows: To the solution of 28.3 g of 5-aminopyridine-2-carboxylic acid methyl ester in 80 ml of 20% sulfuric acid, cooled to −4°, the solution of 14.31 g of sodium nitrite in 30 ml of water is added dropwise while stirring and maintaining the temperature below 0°. Thereafter the mixture is stirred for 15 minutes below 0° and the mixture of 28 g of potassium thiocyanate and 8 g of cuprous thiocyanate is added portionwise to said solution. Each addition causes evolution of gas and a black oil to separate. With continued stirring the oil again dissolves and the solution is stirred for 3 hours. It is extracted with methylene chloride, the extract filtered and evaporated, to yield the 5-thiocyanatopyridine-2-carboxylic acid methyl ester.

To the solution of 25.2 g thereof in 250 ml of methanol 5 g of sodium borohydride are added in small portions during 15 minuted while maintaining the temperature from −7° to about 15°. After 10 minutes the mixture is evaporated, the residue taken up in 5% hydrochloric acid and methylene chloride, the organic phase washed with water, dried and evaporated, to give the 5-mercaptopyridine-2-carboxylic acid methyl ester.

To the solution of 21.8 g of methyl m-trifluoromethylphenylacetate in 450 ml of carbon tetrachloride a portion of 18.7 g of N-bromosuccinimide is added along with several drops of triethylamine and a pinch of azobisisobutyronitrile. The mixture is warmed to reflux with a 250 watt incandescent bulb and a precipitate is formed. Thereupon the reminder of N-bromosuccinimide is added, the light removed and the solution stirred for 3 hours. It is cooled in an ice bath and the solid formed removed by filtration. The filtrate is evaporated the residue dissolved in diethyl ether-water and the organic phase washed with aqueous sodium bicarbonate and water. It is dried, evaporated, the residue distilled and the fraction boiling at 85°–88°/0.4 mmHg collected, to yield the methyl α-bromo-m-trifluoromethylphenylacetate.

EXAMPLE 12

According to the methods of the previous examples, advantageously Examples 7 to 11, the following compounds of Formula II are prepared from equivalent amounts of the corresponding starting materials: X=S

| No. | R | R' | $C_mH_{2m-1}$ | Salt | m.p. °C. |
|---|---|---|---|---|---|
| 1 | Cl | H | CH—(CH$_2$)$_2$ | — | 115–117 |
| 2 | phenyl | H | CH | — | 169–171 |
| 3 | m-CH$_3$—C$_6$H$_4$ | H | " | — | 143–145 |
| 4 | p-CH$_3$—C$_6$H$_4$ | H | " | Na | 286–289 |
| 5 | p-CH$_3$O—C$_6$H$_4$ | H | " | " | 276–280 |
| 6 | m-F—C$_6$H$_4$ | H | " | — | 155–157 |
| 7 | p-F—C$_6$H$_4$ | H | " | Na | 280–286 |
| 8 | o-Cl—C$_6$H$_4$ | H | " | — | 155–157 |
| 9 | m-Cl—C$_6$H$_4$ | H | C—CH$_3$ | — | 120–123 |
| 10 | p-Cl—C$_6$H$_4$ | H | CH | — | 153–155 |
| 11 | " | H | C—n-C$_3$H$_7$ | — | 142–144 |
| 12 | o,o-Cl$_2$—C$_6$H$_3$ | H | CH | Na | 305–310 |
| 13 | o,p-Cl$_2$—C$_6$H$_3$ | H | " | " | 257–260 |
| 14 | m,p-Cl$_2$—C$_6$H$_3$ | H | " | " | 256–258 |
| 15 | m-Br—C$_6$H$_4$ | H | " | " | 260–265 |
| 16 | p-Br—C$_6$H$_4$ | H | " | " | 285–288 |
| 17 | m-CF$_3$—C$_6$H$_4$ | H | " | " | 117–119 |
| 18 | " | H | C—CH$_3$ | — | 114–116 |
| 19 | " | H | C—n-C$_3$H$_7$ | — | 124–127 |
| 20 | " | COOH | CH | — | 190–195 |
| 21 | m-CN—C$_6$H$_4$ | H | " | Na | 229–231 |
| 22 | phenyl | H | CH—CH$_2$ | — | 111–113 |
| 23 | " | H | CH—(CH$_2$)$_2$ | — | 100–103 |

EXAMPLE 13

Preparation of 10,000 tablets each containing 100 mg of the active ingredient:

| Formula: | |
|---|---|
| 5-(n-butylmercapto)-pyridine-2-carboxylic acid | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Analogously tablets are prepared, which contain one of the remaining compounds of the previous examples.

EXAMPLE 14

To the solution obtained from 1.6 g of sodium and 25 ml of anhydrous ethanol 4.2 g of ethanethiol are added at 10° and the mixture is stirred for 15 minutes. Thereupon 16.5 g of 5-(3-chloropropoxy)-2-pyridine carboxylic acid methyl ester (Example 2) in 10 ml of ethanol are added and the mixture is stirred for 48 hours at ambient temperature. It is diluted with chloroform, filtered and the filtrate evaporated. The residue is taken up in diethyl ether, the solution again filtered and the filtrate acidified with ethereal hydrogen chloride. The precipitate formed is collected and recrystallized from ethyl acetate to yield the ethyl 5-(3-ethylmercaptopropoxy)-2-pyridine carboxylate hydrochloride, melting at 95°–97°.

It can be hydrolyzed to the free acid as shown in Example 2.

EXAMPLE 15

The solution of 4.6 g of m-trifluoromethylbenzylmercaptan in 30 ml of dimethylformamide is added to the slurry of 1.08 g of 50% sodium hydride in mineral oil (washed 2 times with hexane), under nitrogen while stirring at room temperature. After several minutes, a clear yellow solution is obtained, which is combined with that of 5.0 g of 3-nitro-2,5-pyridinedicarboxylic acid dimethyl ester in 50 ml of dimethylformamide. The mixture is warmed on the steam bath for 30 minutes at 90° and stirred at room temperature overnight. It is acidified with 2 ml of acetic acid and diluted to 400 ml with a mixture of ice and water. The precipitate formed is collected and recrystallized from methanol-diethyl ether (1:1), to yield the 3-(m-trifluoromethylbenzylmercapto)-2,5-pyridine-dicarboxylic acid dimethyl ester melting at 102°–106°.

2.3 g thereof are suspended in 10 ml of methanol and the suspension combined with 13 ml of N aqueous sodium hydroxide and 35 ml of water. The mixture is warmed on the steam bath for 1 hour, cooled and the pH thereof adjusted to 8 with acetic acid. The solution obtained is treated with charcoal, filtered and the pH of the filtrate changed to 2–3 with 6 N hydrochloric acid. The precipitate formed is collected and recrystallized from acetic acid, to yield the corresponding dicarboxylic acid melting at 193°–194°.

The starting material is prepared as follows: 106 g of 50% sodium hydride in mineral oil are washed with hexane under nitrogen and the slurry is suspended in 425 ml of dimethylsulfoxide while stirring, and 328 g of dimethyl malonate are added dropwise at 60°–70°. When the addition is complete, the mixture is stirred for 5 minutes and 120 g of 2,6-dichloro-3-nitropyridine are added in portions. The temperature is allowed to rise to 75° and the solution is warmed on the steam bath overnight. It is cooled with 275 g of ice, diluted to 550 ml with 6 N hydrochloric acid and another 950 ml of ice-water are added. The mixture is extracted with ethyl acetate, the organic phase washed with aqueous sodium bicarbonate and water, dried, evaporated, and the residue crystallized from methanol-diethyl ether (1:10), to yield the 2,6-bis-dimethylmalonyl-3-nitropyridine melting at 88°–92°.

100 g thereof are suspended in 750 ml of ice water and cooled in an ice bath, while 20 ml of 20 N aqueous sodium hydroxide are added, followed by the hot solution of 100 g of potassium permanganate in 480 ml of water, whereupon another 13 ml of 20 N aqueous sodium hydroxide are added. A vigorous reaction occurs initially and when it subsides, the remaining potassium permanganate and sodium hydroxide are added in portions. A total of 515 g of the former and 53 ml of the latter are used. At the end of the addition the temperature is 90°–94° when the mixture is filtered. The residue is transferred back to the reaction vessel, heated with 100 ml of hot water and again filtered. The combined filtrates are acidified with 200 ml of 12 N hydrochloric acid, the solution is evaporated and the residue suspended in toluene. It is taken to dryness again, and dissolved in 1,000 ml of methanol and 40 ml of concentrated sulfuric acid are added. The mixture is heated to reflux for 30 minutes and allowed to stand at room temperature overnight. It is concentrated, the concentrate diluted with water and methylene chloride, the organic phase separated, washed with water and 10% aqueous sodium bicarbonate, dried, evaporated, and the residual oil crystallized from diethyl-ether-ethyl acetate (1:1), to yield the 3-nitro-2,5-pyridinedicarboxylic acid dimethyl ester melting at 82°–86°.

EXAMPLE 16

4.6 g of 1-propanethiol are added dropwise to the suspension of 2.9 g of 50% sodium hydride in mineral oil, washed with hexane, and 60 ml of dimethylformamide while stirring and cooling with ice. The resulting solution is stirred 10 minutes longer after the gas-evolution ceased and the 100° hot solution of 10 g methyl 5-nitro-2-picolinate in 80 ml of dimethylformamide is added all at once. The initially purple-blue mixture is stirred for 90 minutes and allowed to cool to almost room temperature. It is evaporated, the residue taken up in ethyl acetate, the solution washed with 1 N hydrochloric acid and aqueous sodium hydroxide, dried and evaporated. The residual clear oil solidifies on drying and is crystallized from diethyl ether, to yield the 5-n-propylmercapto-2-pyridinecarboxylic acid methyl ester melting at 33°–35°.

5.08 g thereof are suspended in 60 ml of 1 N aqueous sodium hydroxide and the mixture is warmed on the steam bath for 2 hours and stirred at room temperature for 16 hours. The resulting clear solution is filtered, the filtrate acidified with 5.2 ml of 12 N hydrochloric acid, the precipitate collected and recrystallized from ethanol, to yield the 5-n-propylmercapto-2-pyridinecarboxylic acid melting at 101°–102°.

We claim:

1. A compound of the formula

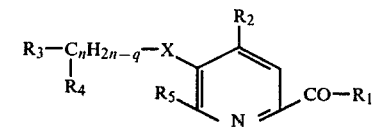

wherein $R_1$ is hydroxy, lower alkoxy, amino, mono- or di-lower alkylamino or hydrazino, $R_2$ is hydrogen, lower alkyl, lower alkoxy or halogeno, X is sulfur, $R_3$ is hydrogen, $R_4$ is hydrogen, hydroxy or $COR_1$, $R_5$ is $R_2$ or $COR_1$, n is an integer from 1 to 7, q is 1 or 3, $(n-q)$ is positive, the N-oxide or a therapeutically useful salt thereof.

2. A compound as claimed in claim 1, in which formula $R_1$ is hydroxy, lower alkoxy, amino, mono- or di-lower alkylamino or hydrazino, each of $R_2$ and $R_5$ is hydrogen, lower alkyl, lower alkoxy or halogeno, X is sulfur, and $R_3R_4C_nH_{2n-q}$ is lower alkyl or lower alkenyl with up to 7 carbon atoms, or a therapeutically useful ammonium, alkali metal or acid addition salt thereof.

3. A compound as claimed in claim 1, and corresponding to the formula

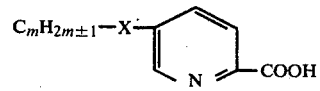

wherein m is an integer from 2 to 5 and X is sulfur, or a therapeutically useful ammonium, alkali metal or acid addition salt thereof.

4. A compound as claimed in claim 3, in which formula $C_mH_{2m\pm1}$ is n-or i-propyl or -butyl, allyl or methallyl and X is sulfur, or a therapeutically useful ammonium, alkali metal or acid addition salt thereof.

5. A compound as claimed in claim 4 and being the 5-(n-butylmercapto)-pyridine-2-carboxylic acid, or a therapeutically useful ammonium, alkali metal or acid addition salt thereof.

6. A hypotensive pharmaceutical composition comprising a hypotensively effective amount of a compound claimed in claim 1, together with a pharmaceutical excipient.

7. A method of treating a mammal suffering from hypertension, which comprises administering to said mammal in need of such treatment enterally or parenterally an effective amount of the composition as claimed in claim 6.

* * * * *